United States Patent [19]

Lonardo

[11] Patent Number: 4,953,569
[45] Date of Patent: Sep. 4, 1990

[54] JOINT PROTECTOR PAD

[75] Inventor: Robert Lonardo, Treasure Island, Fla.

[73] Assignee: L'nard Associates, Inc., St. Petersburg, Fla.

[21] Appl. No.: 194,930

[22] Filed: May 17, 1988

[51] Int. Cl.$^5$ .............................. A61F 13/00
[52] U.S. Cl. .................... 128/892; 128/165; 128/889; 128/894; 2/16; 2/24
[58] Field of Search ............... 128/155, 157, 160, 165, 128/166, 888, 889, 890, 892, 893, 894; 2/16, 24, 411, 414, 421

[56] References Cited

U.S. PATENT DOCUMENTS

| | | | |
|---|---|---|---|
| 2,646,795 | 7/1953 | Scholl | 128/894 |
| 3,011,494 | 12/1961 | McGowan | 128/892 |
| 3,209,750 | 10/1965 | Levitt | 128/894 |
| 3,458,867 | 8/1969 | Moore et al. | 2/16 |
| 4,116,236 | 9/1978 | Albert | 2/24 |
| 4,370,978 | 2/1983 | Palumbo | 128/165 |

FOREIGN PATENT DOCUMENTS 0679089  9/1952  United Kingdom .................... 2/24

Primary Examiner—Randall L. Green
Assistant Examiner—Paul Prebilic
Attorney, Agent, or Firm—Zarley, McKee, Thomte, Voorhees & Sease

[57] ABSTRACT

A pad for preventing skin abrasions at the joints of persons having impaired mobility is disclosed comprising a substantially round pad means having a concave shape and inner and outer sides, a peripheral edge, and a central portion. The outer side of the pad means is comprised of a canvas-like material, and a pad element having the texture of wool fleece and having a central portion comprises the inner side of the pad means and is secured to the canvas-like material. A second pad means is secured to the central portion of the pad element. Elongated strap portions extend in opposite directions from the pad means with outer ends terminating beyond the periphery of the pad means. Suitable fasteners are secured to the outer ends of the strap portions. The strap portions and the second pad means are comprised of foam rubber. A plurality of ventilation holes are provided in the pad means and the pad element.

1 Claim, 1 Drawing Sheet

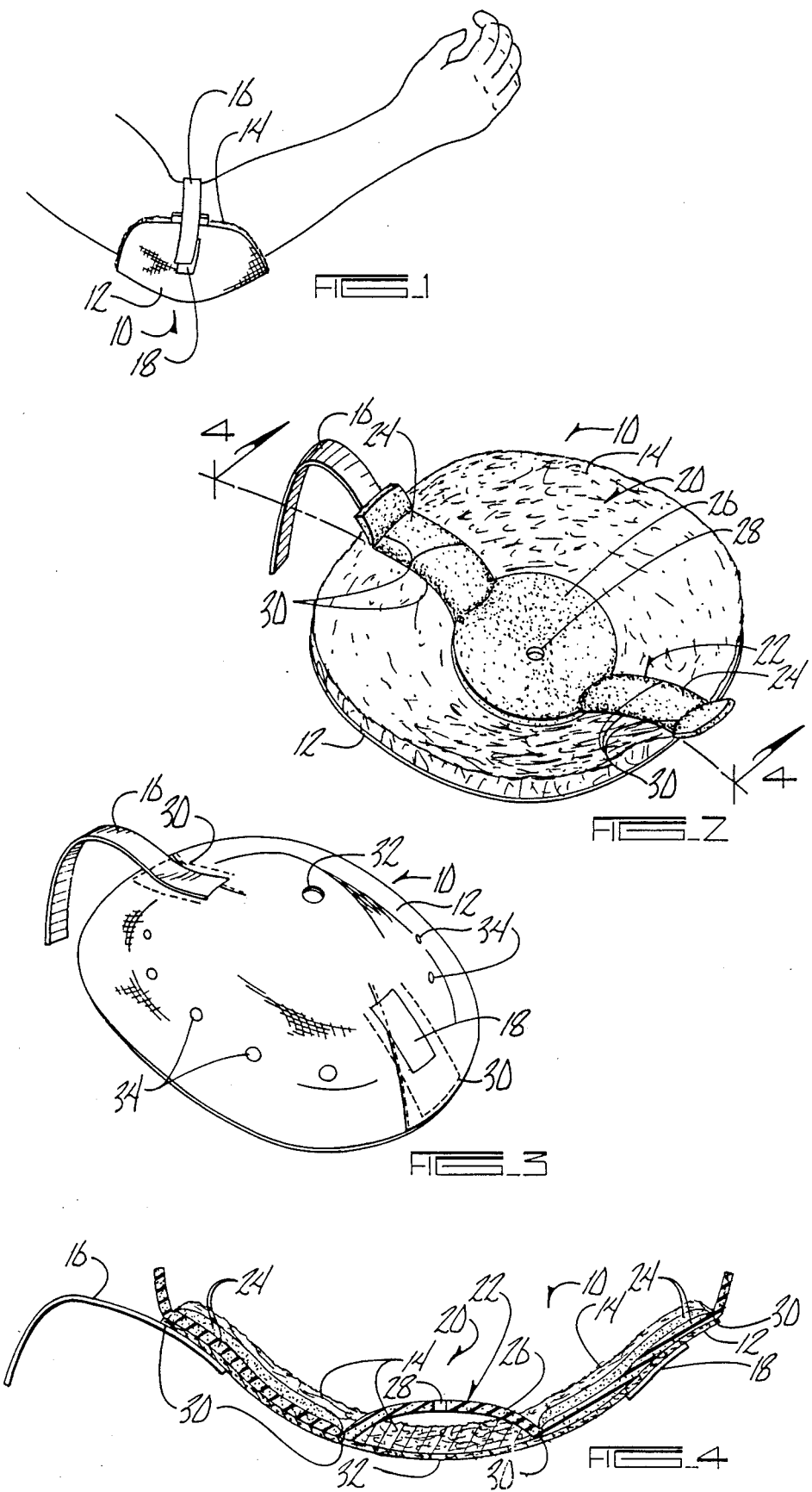

JOINT PROTECTOR PAD

BACKGROUND OF THE INVENTION

Persons who are immobile, for one reason or another, such as those who are bedridden, or confined to wheelchairs, have difficulty with skin abrasions which result from constant rubbing of joints against bed sheets, wheelchairs, or other material. This friction can cause sores and ulcers at the elbows, knees, or ankles.

One method of alleviating this problem is to provide for a pad secured to the joint. A problem which frequently occurs, however, is that the pads slip quite easily out of place. This slipping only aggravates the abrasion upon the skin.

This invention addresses the problem by providing a strip of foam on the inside of the pad to be attached to the joint. The foam prevents slipping, and thereby reduces the chance of further irritation to the skin.

Accordingly, it is an object of the invention to provide a method and means for decreasing skin abrasions in persons who have impaired mobility.

Another object of the invention is to provide a means and method of maintaining protection of the skin regardless of movement of the patient.

A further object is to inhibit any slippage of the protective mechanism while in use on the patient.

Another object is to provide a comfortable means and method of preventing skin abrasions in persons having impaired mobility.

Yet another object is to provide a means of preventing skin abrasions in persons with impaired mobility which provides for ventilation to the skin.

A still further object is to provide a means of preventing slipping of a pad around a joint of a person with impaired mobility which is easily attached to the pad.

SUMMARY OF THE INVENTION

The invention relates to pads which are secured to the joints of persons having impaired mobility, in order to prevent skin abrasions. It provides for a strip of foam to be attached to the inner side of the pad which is placed against a person's joint. The strip adheres to the skin and prevents slippage of the pad, and thereby further reduces the chance of aggravating skin abrasions.

BRIEF DESCRIPTION OF THE DRAWINGS

FIG. 1 is a perspective view of the device of this invention secured to the elbow of the user.

FIG. 2 is a plan view of the pad of this invention showing the interior side of the pad.

FIG. 3 is a plan view of the pad of this invention showing the outer side.

FIG. 4 is a side cross-sectional view taken along line 4—4 of FIG. 2.

DETAILED DESCRIPTION OF THE PREFERRED EMBODIMENT

The numeral 10 shows the pad employed in preventing skin abrasions. In FIG. 1, it is, secured to the elbow of the user. The pad 10 consists of an outer canvas layer 12 as a wear-resistant material which is secured to padding material 14 on the inner side. This padding material 14 is a washable polyester fiber having the texture of wool fleece. The canvas layer 12 and padding material 14 are available under the trademark KODEL. The pad 10 is generally round in shape in order to accommodate the joint of the user. It is secured to the user through a strap 16. Strap 16 is secured to one side of the pad 10 by stitching or the like and includes on at least a portion of its inner surface a mechanism such as a VELCRO, hook and loop fastener to secure it to the other side of the pad 10.

The hooks of the VELCRO are provided on the inner side of at least a portion of strap 16 (not pictured), while secured to the opposite side of pad 10 are the VELCRO loops 18. Thus, the strap 16 is brought around the interior of the joint of the user and is secured on the opposite side at loops 18. Pad 10 includes a concave portion 20 so that the joint may rest comfortably therein.

The invention consists of a foam strip 22 which extends across the padding material 14 on the inner side of the pad 10. Foam rubber is particularly useful because of its ability to adhere to the skin and prevent slippage, while not aggravating the skin and causing further abrasions. This form is specially formulated foam that has modular open cell composition that when compressed acts like tiny suction cups. It is also made of a non-skid adherent construction.

The foam strip, of course, may take any number of shapes and still accomplish its objectives. In this embodiment of the invention, foam strip 22 includes elongated, rectangular portions 24 opposite one another, with a generally circular central portion 26. Included in the circular center portion 26 is a central ventilation hole within the foam strip 28. This encourages passage of air from the outside, for increased comfort. The foam strip 22 may be attached to the padding material 14 in any fashion, and here includes a sewn portion 30 at either end and along the sides of rectangular portions 24.

In FIG. 3, it can be seen that it is preferable to include a central ventilation hole 32 in the canvas layer or outer portion 12, as well. Side holes 34 are further provided in the pad for additional ventilation.

FIG. 4 represents a cross-sectional view showing the sewn portion 30 on the outer periphery of elongated portion 24. As can be seen in this embodiment, the circular central portion 26 of foam strip 22 is allowed to rise up from the padded material 14, further increasing ventilation through central ventilation hole 28.

This embodiment of the invention is presented as an illustration, and is not intended to limit the invention thereby.

Thus, it can be seen that the invention accomplishes all of its objectives.

What is claimed is:

1. A pad for preventing skin abrasions at the joints of persons having impaired mobility, comprising,
    a substantially round pad means having a concave shape and inner and outer sides, a peripheral edge, and a central portion,
    said outer side of said pad means being comprised of a wear-resistant material,
    the inner side of said pad means being comprised of a first pad element extending over substantially all of the wear-resistant material and being permanently secured to said wear-resistant material so as to prevent relative movement therebetween, said first pad element having the texture of wool fleece, and having a central portion,
    a second pad element permanently secured to the central portion of said first pad element to prevent relative movement therebetween and so as to be in covering relation to the central portion, strap means on said pad means for securing the pad means to the person, fastening means on said strap means adapted to be secured together to secure said pad means to the joint of a person wearing the pad means, said second pad element and said strap portions being comprised of foam rubber of modular open cell construction, said strap means being secured to at least the peripheral edge of said pad means, and at least one ventilation hole in said were-resistant material and said second pad element.

* * * * *